United States Patent
Zhang et al.

(10) Patent No.: US 6,574,512 B1
(45) Date of Patent: Jun. 3, 2003

(54) LEAD SYSTEM WITH MAIN LEAD AND TRANSVERSE LEAD

(75) Inventors: Yongxing Zhang, Little Canada, MN (US); Weimin Sun, Plymouth, MN (US); Scott M. Partridge, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/649,769

(22) Filed: Aug. 28, 2000

(51) Int. Cl.[7] .................................................. A61N 1/05
(52) U.S. Cl. ......................................................... 607/122
(58) Field of Search ............................... 607/115, 116, 607/119, 122, 123, 126; 600/372–375, 377, 381

(56) References Cited

U.S. PATENT DOCUMENTS

| | | | |
|---|---|---|---|
| 3,865,118 A | 2/1975 | Bures | 128/404 |
| 3,939,843 A | 2/1976 | Smyth | 128/404 |
| 4,030,509 A | 6/1977 | Heilman et al. | 128/419 D |
| 4,057,067 A * | 11/1977 | Lajos | 607/123 |
| 4,289,144 A * | 9/1981 | Gilman | 607/123 |
| 4,351,345 A | 9/1982 | Carney | 128/786 |
| 4,458,677 A * | 7/1984 | McCorkle, Jr. | 607/123 |
| 4,497,326 A | 2/1985 | Curry | 128/785 |
| 4,567,901 A * | 2/1986 | Harris | 607/123 |
| 4,662,382 A | 5/1987 | Sluetz et al. | 128/785 |
| 4,858,611 A | 8/1989 | Elliott | 128/419 P |
| 4,884,567 A | 12/1989 | Elliott et al. | 128/303 R |
| 4,946,457 A | 8/1990 | Elliott | 606/1 |
| 5,003,990 A | 4/1991 | Osypka | 128/772 |
| 5,044,375 A * | 9/1991 | Bach et al. | 600/374 |
| 5,122,115 A | 6/1992 | Marks | 604/53 |
| 5,209,229 A | 5/1993 | Gilli | 128/419 D |
| 5,261,395 A | 11/1993 | Oleen et al. | 607/15 |
| 5,269,319 A * | 12/1993 | Schulte et al. | 607/123 |
| 5,304,218 A | 4/1994 | Alferness | 607/122 |
| 5,466,253 A | 11/1995 | Doan | 607/122 |
| 5,476,498 A | 12/1995 | Ayers | 607/122 |
| 5,545,203 A | 8/1996 | Doan | 607/122 |
| 5,643,338 A | 7/1997 | Bornzin et al. | 607/123 |

(List continued on next page.)

*Primary Examiner*—Kennedy Schaetzle
*Assistant Examiner*—Kristen Droesch
(74) *Attorney, Agent, or Firm*—Schwegman, Lundberg, Woessner & Kluth, P.A.

(57) ABSTRACT

A lead comprising both a main lead and a transverse lead. The main lead includes a main lead body with a longitudinal axis and at least one electrode. The Transverse lead includes a transverse lead body and at least one electrode, where the transverse lead body extends laterally from the main lead body and curves around the longitudinal axis of the main lead body to partially encircle at least a portion of the main lead. In one embodiment, the transverse lead is adapted to press the at least one electrode on the transverse lead against endocardial tissue. At least a portion of the main lead and at least a portion of the transverse lead are both adapted to be housed within and pass through an implant catheter. In an alternative embodiment, there is a lead system which comprises a first lead and a second lead, where the second lead includes a sleeve, where the first lead is adapted to move through the sleeve to attach the first lead to the second lead.

26 Claims, 14 Drawing Sheets

U.S. PATENT DOCUMENTS

| | | | |
|---|---|---|---|
| 5,674,274 A | 10/1997 | Morgan et al. | 607/123 |
| 5,683,447 A | 11/1997 | Bush et al. | 607/126 |
| 5,776,072 A | 7/1998 | Hsu et al. | 600/518 |
| 5,782,898 A | 7/1998 | Dahl et al. | 607/119 |
| 5,797,967 A | 8/1998 | KenKnight | 607/4 |
| 5,855,995 A | 1/1999 | Haq et al. | 428/210 |
| 5,861,013 A | 1/1999 | Peck et al. | 607/28 |
| 5,871,508 A | 2/1999 | Thompson et al. | 607/9 |
| 5,871,512 A | 2/1999 | Hemming et al. | 607/28 |
| 5,871,530 A | 2/1999 | Williams et al. | 607/122 |
| 5,873,898 A | 2/1999 | Hemming et al. | 607/28 |
| 5,885,221 A | 3/1999 | Hsu et al. | 600/515 |
| 5,902,331 A | 5/1999 | Bonner et al. | 607/122 |
| 5,922,014 A | 7/1999 | Warman et al. | 607/123 |
| 5,925,073 A | 7/1999 | Chastain et al. | 607/122 |
| 5,935,160 A | 8/1999 | Auricchio et al. | 607/122 |
| 5,968,087 A | 10/1999 | Hess et al. | 607/127 |
| 6,006,122 A * | 12/1999 | Smits | 600/374 |
| 6,006,137 A | 12/1999 | Williams | 607/119 |
| 6,021,354 A | 2/2000 | Warman et al. | 607/123 |
| 6,055,457 A | 4/2000 | Bonner | 607/126 |
| 6,058,332 A | 5/2000 | Dahl | 607/119 |
| 6,061,594 A | 5/2000 | Zhu et al. | 607/28 |
| 6,076,014 A | 6/2000 | Alt | 607/4 |
| 6,083,247 A * | 7/2000 | Rutten et al. | 607/123 |
| 6,096,064 A | 8/2000 | Routh | 607/9 |
| 6,119,043 A | 9/2000 | Hsu et al. | 607/123 |
| 6,148,238 A * | 11/2000 | Rutten | 607/126 |
| 6,278,897 B1 * | 8/2001 | Rutten et al. | 607/122 |

* cited by examiner

LEAD SYSTEM WITH MAIN LEAD AND TRANSVERSE LEAD

FIELD OF THE INVENTION

The present invention relates generally to cardiac leads. More particularly, the present invention pertains to a cardiac lead system having multiple leads.

BACKGROUND

Electrodes implanted in or about the heart have been used to reverse (i.e., defibrillate or cardiovert) certain life threatening arrhythmias by applying electrical energy through the electrodes to return the heart to a normal rhythm. Electrodes have also been used to sense and deliver pacing pulses to the atrium and ventricle. The electrode in the atrium senses the electrical signals that trigger the heartbeat. The electrode detects abnormally slow (bradycardia) or abnormally fast (tachycardia) heartbeats. In response to the sensed bradycardia or tachycardia condition, a pulse generator produces pulses or signals to correct the condition. The same node used to sense the condition is also used in the process of delivering a corrective pulse or signal from the pulse generator of the pacemaker.

There are four main types of pulses which are delivered by a pulse generator. Two of the signals or pulses are for pacing the heart. First of all, there is a pulse for pacing the heart when it is beating too slowly, and the pulse triggers the heart beat. The pulses are delivered at a rate to increase the heart rate to a desired level. The second type of pacing, called antitachycardia pacing, is used on a heart that is beating too fast. In antitachycardia pacing, the pacing pulses are delivered initially at a rate faster than the beating heart. The rate of the pulses is then slowed until the heart rate is at a desired level. The third and fourth type of pulses are used when the heart is beating too fast and the heart is fibrillating. The third type is called cardioversion. This is delivery of a relatively low energy shock, typically in the range of 0.75 to 1 joule, to the heart. The fourth type of pulse or signal is a defibrillation signal which is the delivery of a high energy shock, typically up to 34 joules, to the heart.

Sick sinus syndrome and symptomatic AV block constitute the major reasons for insertion of cardiac pacemakers today. Cardiac pacing may be performed by the transvenous method or by electrodes implanted directly onto the epicardium, where transvenous pacing may be temporary or permanent. In temporary transvenous pacing, an electrode lead is introduced into a peripheral vein and fluoroscopically positioned against the endocardium. The external terminals of the leads are connected to an external cardiac pacemaker which has an adjustable rate and milliamperage control. Temporary transvenous pacing is utilized prior to insertion of a permanent pacing system and in situations in which the indication for pacing is judged to be reversible (drug-induced AV block or bradycardia) or possibly irreversible and progressive (AV and bundle branch blocks associated with myocardial infarction).

Permanent transvenous pacing systems are implanted under sterile surgical conditions. An electrode lead is generally positioned in the right ventricle and/or in the right atrium through a subclavian vein, and the proximal electrode terminals are attached to a pacemaker which is implanted subcutaneously. Some patients require a pacing system to correct an abnormally slow heart (bradycardia condition) as well as a defibrillation system to detect when the heart starts beating abnormally fast (tachycardia condition) and to defibrillate or deliver a pulse to the heart to correct the abnormally fast heartbeat. In the past, a common practice for a patient having both of these conditions would be to provide two different leads attached to the heart. One would be implanted for delivering pacing signals to the heart to correct for the bradycardia condition. A separate lead would be implanted to sense a fast beating heart and defibrillate the heart to correct for the tachycardia condition. One lead is placed in the atrium and the other lead is placed in the ventricle.

Having two separate leads implanted within the heart is undesirable for many reasons. Among the many reasons is that the implantation procedure for implanting two leads is more complex and also takes a longer time when compared to the complexity and time needed to implant a single lead. In addition, two leads may interact with one another after implantation or in vivo which can result in dislodgment of one or both of the leads. In vivo interaction may also cause abrasion of the insulative layer along the lead which can result in an electrical failure of one or both of the leads. Another problem is that as more leads are implanted in the heart, it can become increasingly difficult to add additional leads. Two separate leads also increase the risk of infection and may result in additional health care costs associated with implantation and follow-up. Thus, there is a need for a lead which allows for both energy delivery to and sensing from both atrial locations and ventricular locations while reducing the detrimental interactions between the leads that perform these functions.

SUMMARY

A single-pass endocardial lead is provided which is adapted for implantation on or about the heart and is adapted for connection to a system for monitoring or stimulating cardiac activity and includes a lead body. In one embodiment, the lead includes a main lead and a transverse lead, where the both leads have at least one electrode each. The transverse lead extends laterally from the main lead at a point which is between the distal and proximal ends of the main lead and curves around the longitudinal axis of the main lead to partially encircle at least a portion of the main lead. In an additional embodiment, there is provided a lead system which includes a first lead and a second lead. Both the first and the second lead include at least one electrode, and the second lead further includes a sleeve through which the first lead is adapted to move so as to attach the first lead to the second lead. These lead structures allows for both electrical energy pulses to be delivered to and cardiac signal to be sensed from both atrial locations and ventricular locations while reducing the detrimental interactions between the leads that perform these functions.

In one embodiment, the lead comprises the main lead and the transverse lead. The main lead includes a main lead body with a longitudinal axis and at least one electrode, where the main lead body extends from a proximal end to a distal end and is adapted to carry signals to and from the heart. The transverse lead includes a transverse lead body and at least one electrode, where the transverse lead body is also adapted to carry signals to and from the heart. The transverse lead body extends laterally from the main lead body between the proximal end and the distal end and curves around the longitudinal axis to partially encircle at least a portion of the main lead. In one embodiment, the transverse lead is adapted to press the at least one electrode on the transverse lead against endocardial tissue.

In one embodiment, the main lead and the transverse lead are adapted to be implanted into the heart, where the proximal end of the main lead is releasably coupled to an implantable pulse generator to allow for cardiac signals to be sensed from the heart and for energy pulses to be delivered to the heart through the electrodes positioned on the main lead and the transverse lead. In one embodiment, the main lead is implanted with its distal end positioned in the right ventricle and the transverse lead positioned in the right atrium. Alternatively, the main lead is implanted with its distal end positioned in the right ventricle or right atrium and the transverse lead positioned in at least partially within the coronary sinus vein with its electrodes adjacent the left atrium and or the left ventricle.

In one embodiment, at least a portion of the main lead and at least a portion of the transverse lead are both adapted to be housed within an implant catheter. After inserting the implant catheter containing at least a portion of the main lead and the transverse lead, the main lead and the transverse lead are passed through the catheter. Use of the implant catheter to deliver the main and transverse leads allows for greater ease in implanting the lead as compared to not using the catheter.

In an alternative embodiment, the lead system comprises a first lead and a second lead. The first lead includes a lead body and at least one electrode, and the second lead includes at least one electrode and a sleeve, where the first lead is adapted to move through the sleeve to attach the first lead to the second lead. Both the first lead and the second lead are adapted to sense cardiac signals from and deliver electrical pulses to a heart. In one embodiment, the sleeve is coupled to the external surface of the second lead body. In alternative embodiment, the sleeve is an integral part of (i.e., formed with) the second lead body.

In one embodiment, the sleeve is a tubular segment having an inner surface defining an opening adapted to receive and pass at least a portion of the lead body of the first lead. In one embodiment, the sleeve on the second lead is passed over at least a portion of the first lead. The first lead is then inserted, or implanted, into a heart. The second lead is then inserted into the heart by passing the sleeve over at least a portion of the inserted first lead. In one embodiment, a guidewire is first inserted into the heart. The first lead is then advanced over the guidewire to position the first lead in the heart, where the first lead has a lumen which extends between a distal end and a proximal end. Alternatively, the lumen of the first lead extends only partially through the lead body of the first lead near or at the distal end to allow for an over-the-wire insertion of the first lead.

The sleeve is then passed over at least a portion of the inserted first lead to insert the second lead into the heart. In one embodiment, a stylet is used to advance the second lead into the heart. The proximal ends of the leads are then held and the stylet and guidewire withdrawn. The leads are then connected to the implantable pulse generator for use in the patient.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
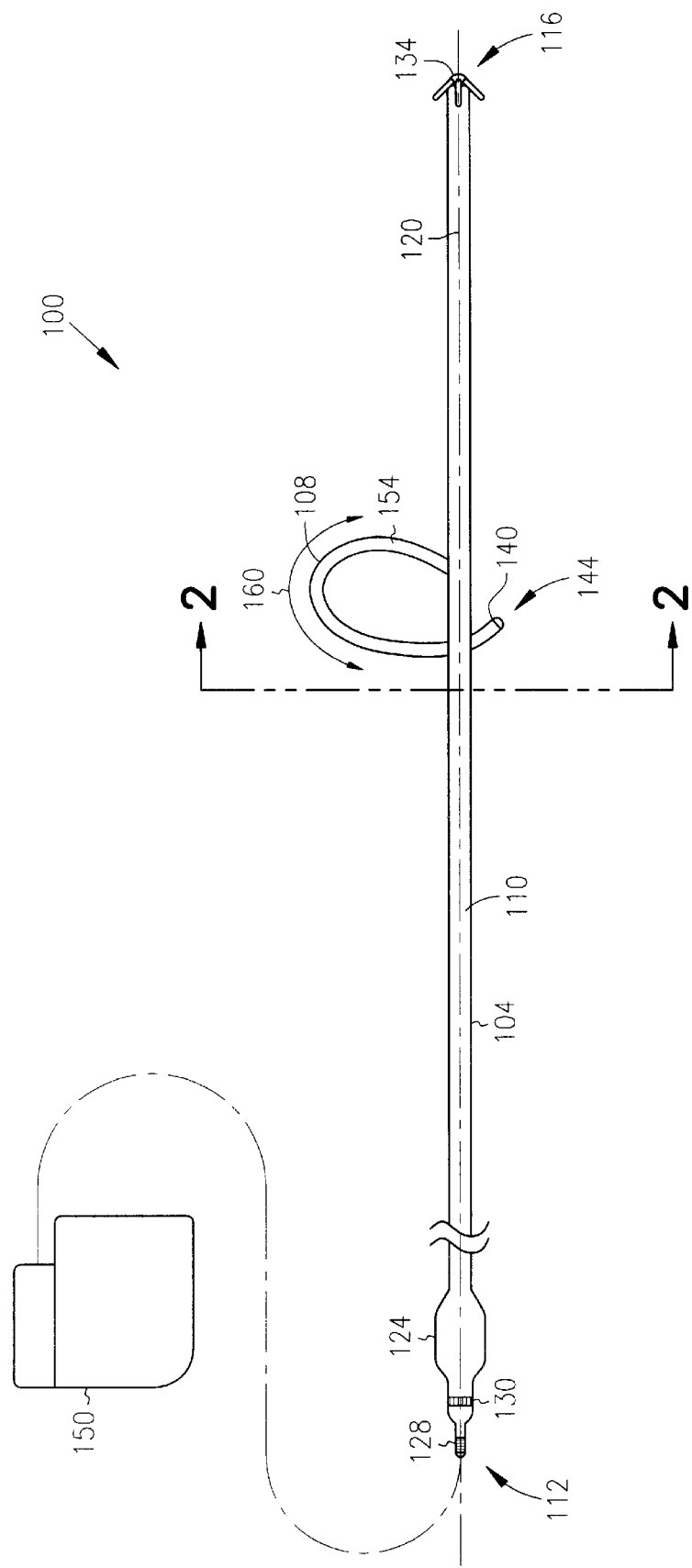
FIG. 1 shows a side view of one exemplary embodiment of a lead according to the present subject matter.

FIG. 1 one exemplary embodiment of a lead 100 according to the present subject matter. The lead 100 includes a main lead 104 and a transverse lead 108. The main lead includes a main lead body 110 which extends from a proximal end 112 to a distal end 116 along a longitudinal axis 120. The main lead 104 further includes a lead connector 124 having one or more connector terminals near the proximal end 112. In one embodiment, the lead connector and connector terminals are designed to conform with International Standards (e.g., IS-1 UNI or IS-1 BI).

In one embodiment, the main lead 104 has a connector terminal pin 128 and a connector terminal ring 130. The main lead body 110 also includes at least one electrode, where the one or more electrodes are any combination of pacing/sensing electrode and/or defibrillation electrodes. In one embodiment, the main lead 104 includes a distal tip pace/sense electrode 134 which is located at or adjacent the distal end 116 of the main lead 104. A lead conductor connects the distal tip pace/sense electrode 134 with a connector terminal (e.g., the connector terminal pin 128 or the connector terminal ring 130). The lead conductor has either a linear or a coil shape, where the coil shape allows for a stylet lumen to be formed.

The lead 100 also includes transverse lead 108. The transverse lead 108 extends away from the main lead body 110 at a point between the proximal end 112 and the distal end 116 of the main lead 104. In the embodiment shown in FIG. 1, the main lead 104 and the transverse lead 108 are shown in a relaxed, or a normal unstressed, state. In one embodiment, the transverse lead 108 extends latterly from the main lead body 110 and curves around the longitudinal axis 120 of the main lead 104 to partially encircle at least a portion of the main lead 104, as will be described more fully below.

The transverse lead 108 further includes at least one electrode. In one embodiment, the transverse lead 108 includes a first pacing/sensing electrode 140 which is coupled by a lead conductor to a connector terminal (e.g., the connector terminal pin 128 or the connector terminal ring 130) near the proximal end 112 of the main lead 104. In one embodiment, the first pacing/sensing electrode 140 is located at or adjacent a distal end 144 of the transverse lead 108. In one exemplary embodiment, the first pacing/sensing electrode 140 is a ring electrode positioned proximal a distal end 144 of the transverse lead 108, where the ring electrode at least partially or completely encircles the lead body 110.

In one embodiment, the lead connector 124 is adapted to be releasably coupled to a connector block of an implantable pulse generator 150. In one embodiment, the implantable pulse generator 150 contain electronics to sense cardiac signals from the heart through the use of the electrodes on the lead 100, where the cardiac signals include indications of cardiac cycles. In one embodiment, a unipolar cardiac signal is sensed between the distal tip pace/sense electrode 134 on the main lead 104 and the housing of the implantable pulse generator 150. A unipolar cardiac signal is also sensed between the first pacing/sensing electrode 140 on the transverse lead 108 and the housing of the implantable pulse generator 150. Alteratively, additional pacing/sensing electrodes are provided on the main lead 104 and/or the transverse lead 108 to allow for bipolar cardiac signals to be sensed from the heart.

In one embodiment, the distal tip pace/sense electrode 134 and the first pacing/sensing electrode 140 are porous electrodes, where porous electrodes include woven mesh electrodes or electrodes created by sintering metal powders or microspheres onto metal substrates. Alternatively, the distal tip pace/sense electrode 134 and the first pacing/ sensing electrode 140 are ring electrodes, as previously described. The pacing/sensing electrodes are created from either platinum, platinum-iridium alloys or alloys which can include cobalt, iron, chromium, molybdenum, nickel and/or manganese.

In one embodiment, the lead 100 is formed of a biocompatible polymer such as silicone rubber and/or polyurethane. The lead 100 further includes one or more lumens which are adapted to receive a stylet for guiding and implanting the lead 100, including the main lead 104 and the transverse lead 108. In one embodiment, the lead 100 includes a first lumen, where the first lumen extends from an opening at the proximal end 112 of the main lead 104 to the distal end 116 of the main lead 104 to allow the main lead 104 to be controlled through the use of the stylet. As previously discussed, in one exemplary embodiment the first lumen is formed from the lead conductor for the distal tip pace/sense electrode 134 on the main lead 104.

The main lead 104 and the transverse lead 108 of lead 100 each has a length and a shape that is adapted to be implanted into any number of size hearts. The length of the main lead will be dependent upon the size of the patient. In one embodiment, the length of the main lead is sufficient to allow the distal end 116 of the main lead 104 to be implanted into the apex of the right ventricle. The main lead 104 is attached to the endocardium either actively or passively. For active fixation, the main lead 104 has an active screw at the distal end 116 of the lead 100, where the screw is either retractable or not retractable, and either electrically active or not electrically active. For passive fixation, tines are positioned behind the electrode and are adapted to become entangled/entrapped within the trabeculae of the right atrial appendage and right ventricle.

In one embodiment, the transverse lead 108 is positioned on the main lead 104 so that when the main lead 104 is implanted in the right ventricle, the transverse lead 108 is positioned in the supraventricular region of the heart. In one embodiment, when the distal end 116 of the main lead 104 is positioned in the right ventricle, the transverse lead 108 is located within the right atrium. This allows for cardiac signals to be sensed from and for pacing pulses to be delivered both the right atrium and the right ventricle. In an alternative embodiment, the transverse lead 108 is positioned at least partially within one or more coronary veins to allow for the transverse lead 108 to be positioned adjacent either the left atrium and/or the left ventricle. This allows for cardiac signals to be sensed from and for pacing pulses to be delivered either the left atrium, left ventricle and/or the right ventricle.

Figure 2:
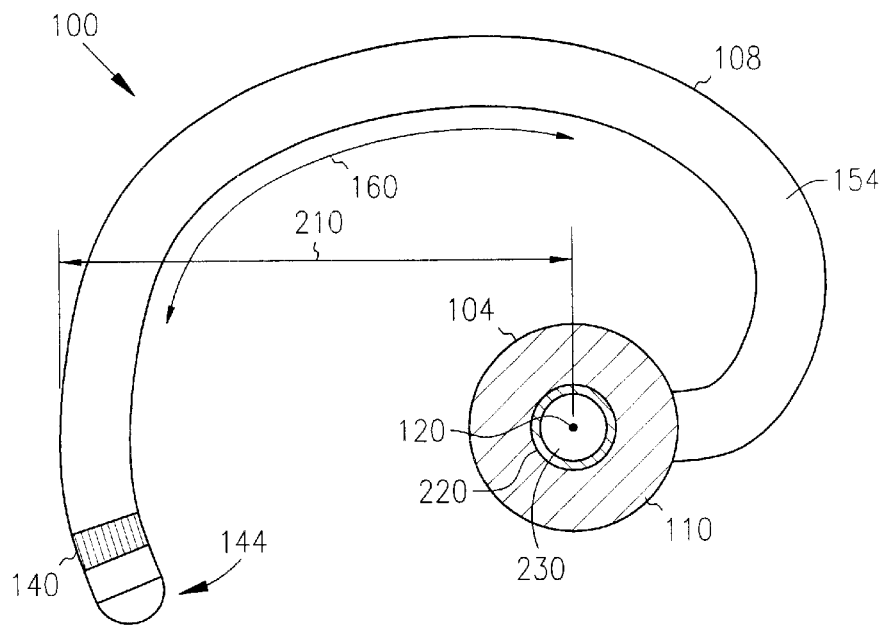
FIG. 2 shows a view of the lead system of FIG. 1 taken along the lines 2—2.
Figure 3:
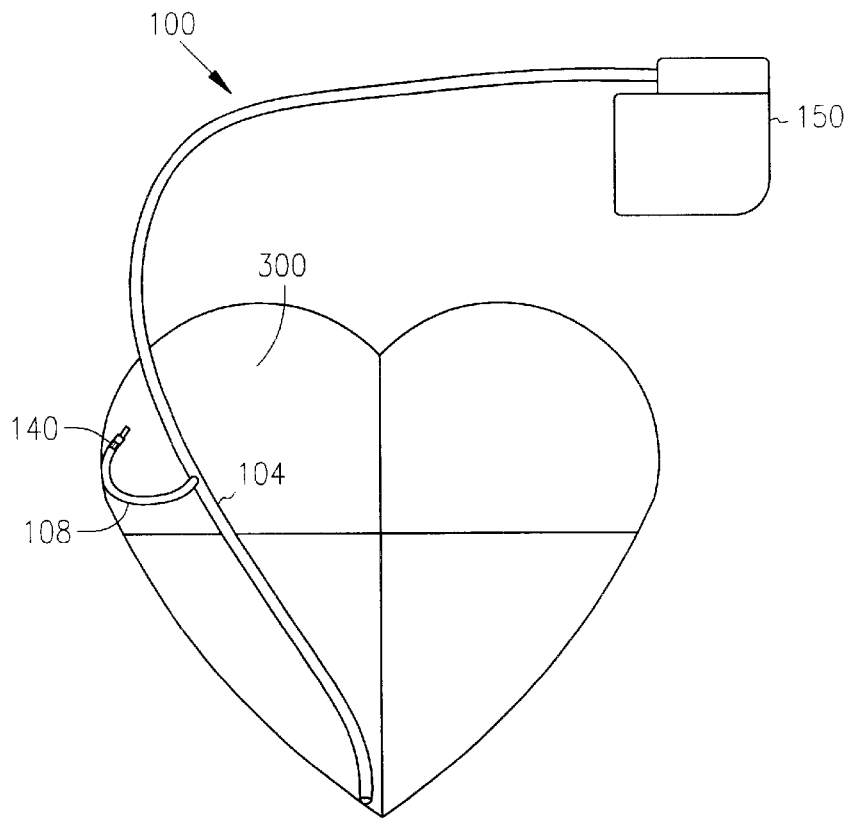
FIG. 3 shows one exemplary embodiment of a lead system according to the present subject matter implanted into a heart from which segments have been removed to show details.

As previously described, the transverse lead 108 extends from the main lead body 110 and curves around the longitudinal axis 120 of the main lead 104 to partially encircle at least a portion of the main lead 104. In one embodiment, the transverse lead 108 includes a transverse lead body 154 having a curve which forms a spiral 160. FIGS. 2 and 3 show exemplary embodiments of the transverse lead 108. FIG. 2 shows a view of the lead system 100 taken along the lines 2—2 in FIG. 1. The embodiment of the transverse lead 108 in FIG. 2 shows the transverse lead 108 having the curve which forms the spiral 160 around the longitudinal axis 120 of the main lead 104. In one embodiment, the transverse lead 108 is adapted to press the at least one electrode (e.g., the first pacing/sensing electrode 140) against endocardial tissue. For example, the spiral 160 on the transverse lead 108 has a radius of curvature 210 that is sufficient to press the transverse lead body 154 against endocardial tissue. FIG. 3 shows one exemplary embodiment in which the transverse lead 108 curves away from the main lead 104 to engage and press the first pacing/sensing electrode 140 against the right atrium 300. In this embodiment, the lead 100 is used to sense cardiac signals from and supply pacing pulses to both the right atrium and the right ventricle. FIG. 2 also shows one embodiment of a lead conductor 220 having a coil shape which forms stylet lumen 230.

Figure 4:
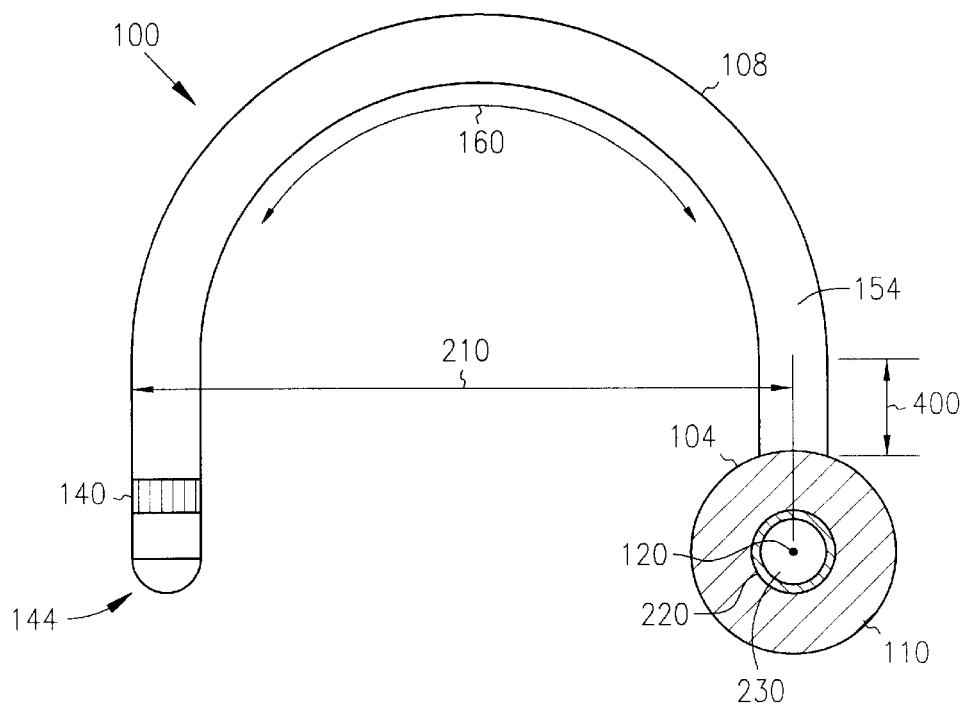
FIG. 4 shows a cross-sectional view of an one exemplary embodiment of a lead according to the present subject matter.

FIG. 4 shows an alternative embodiment of the transverse lead 108. Transverse lead 108 includes the elements shown in FIG. 2, but the transverse lead body 154 further includes segment 400 which extends away from the longitudinal axis 120 of the main lead body 110. By way of example, the segment 400 extends linearly from the main lead body 110 at approximately a 90 degree angle with respect to the longitudinal axis 120.

As previously mentioned, the transverse lead body 154 encircles at least a portion the main lead body 110. In one embodiment, the transverse lead body 154 encircles about one-fourth to five-sixths of the main lead body 110 relative the longitudinal axis 120. In additional embodiments, the transverse lead body 154 encircles the main lead body 110 one or more times. For example, FIG. 2 shows an embodiment in which the transverse lead body 154 encircles approximately one-half the main lead body 110 relative the longitudinal axis 120. FIG. 4 shows an embodiment in which the transverse lead body 154 encircles approximately one-fourth the main lead body 110 relative the longitudinal axis 120.

Figure 5:
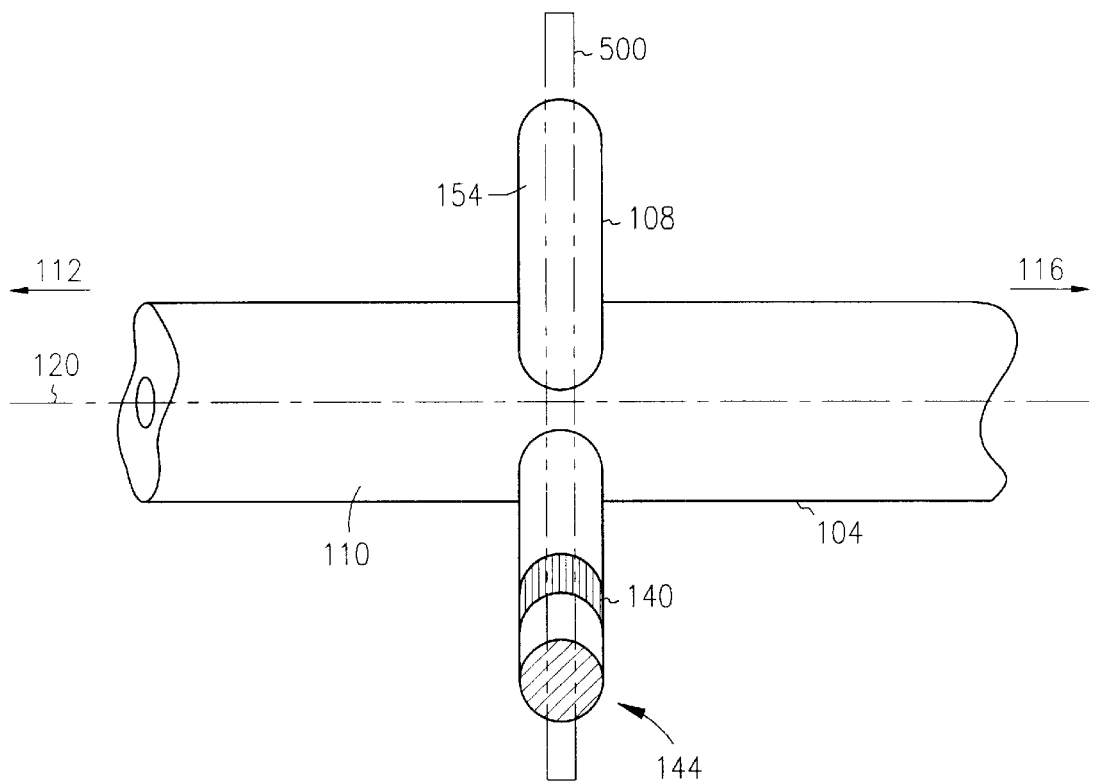
FIG. 5 shows a transverse lead and a segment of a main lead of a main lead according to one embodiment of the present subject matter.
Figure 6:
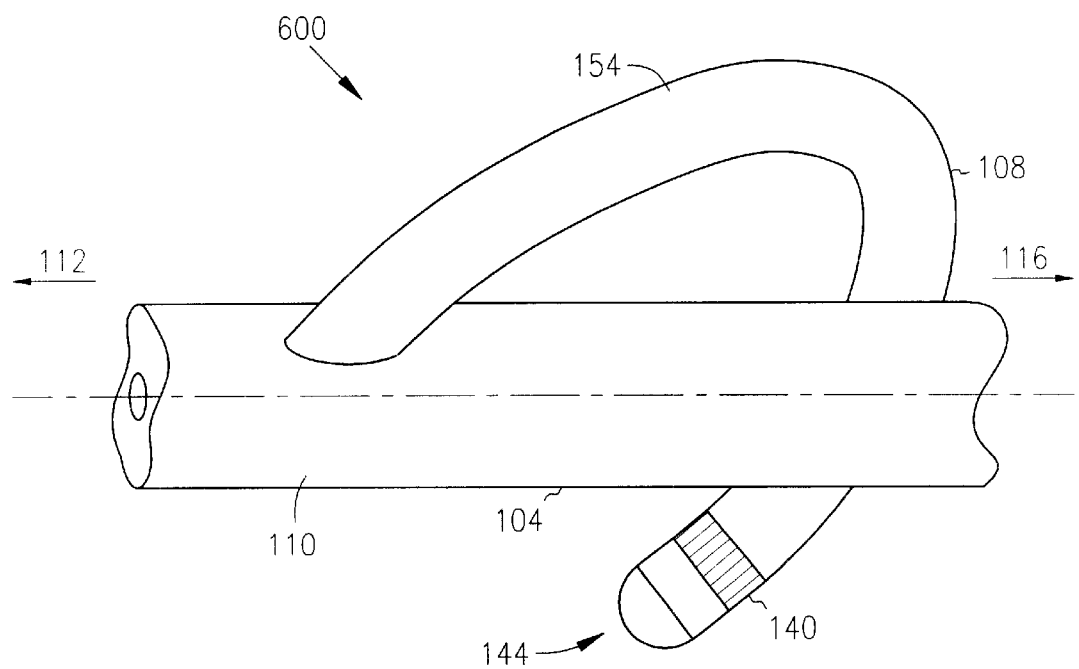
FIG. 6 shows a transverse lead and a segment of a main lead of a main lead according to one embodiment of the present subject matter.
Figure 7:
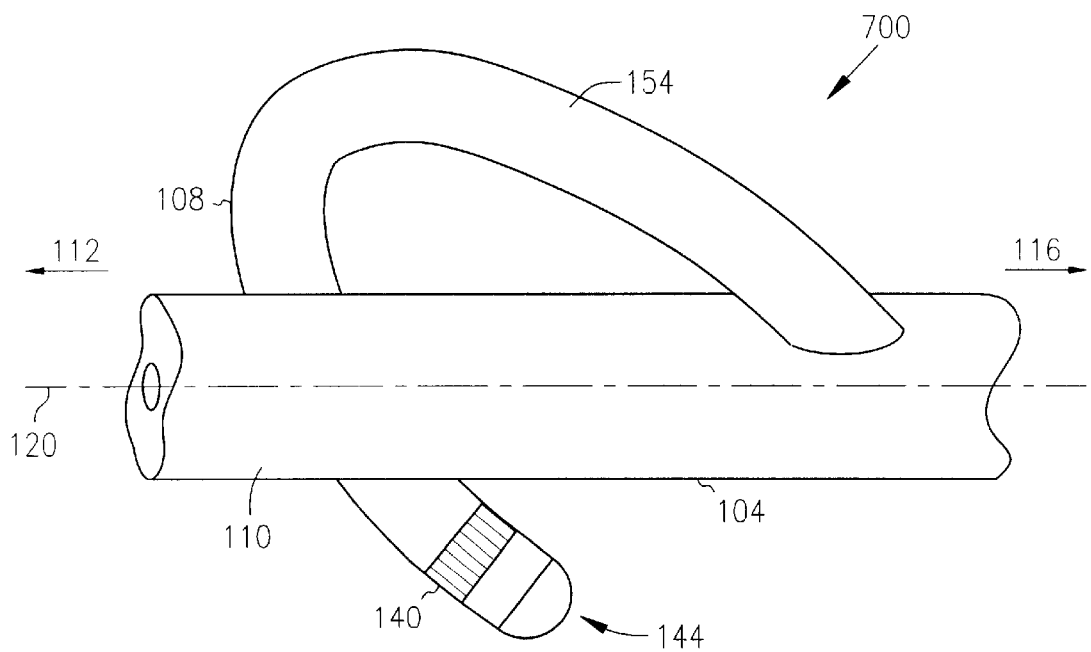
FIG. 7 shows a transverse lead and a segment of a main lead of a main lead according to one embodiment of the present subject matter.

The transverse lead body 154 extends laterally from the main lead body 110 at any number of angles relative the longitudinal axis 120 of the main lead body 110. The transverse lead body 154 also takes on any number of shapes. In one exemplary embodiment the transverse lead 108 forms a plane that is perpendicular to the longitudinal axis of the main lead body. An example of the perpendicular plane formed by the transverse lead 108 is shown in FIG. 5, where the perpendicular plane is shown generally at 500. In an additional example, the transverse lead 108 remains in a first plane 600 as the lead 108 extends from the main lead body 110 first towards the distal end 116 and then curves back towards the proximal end 112, as shown in FIG. 6. In an alternative embodiment, the transverse lead 108 remains in a second plane 700 as the lead 108 first extends from the main lead body 110 towards the proximal end 112 and then curves back towards the distal end 116, as shown in FIG. 7.

Figure 8:
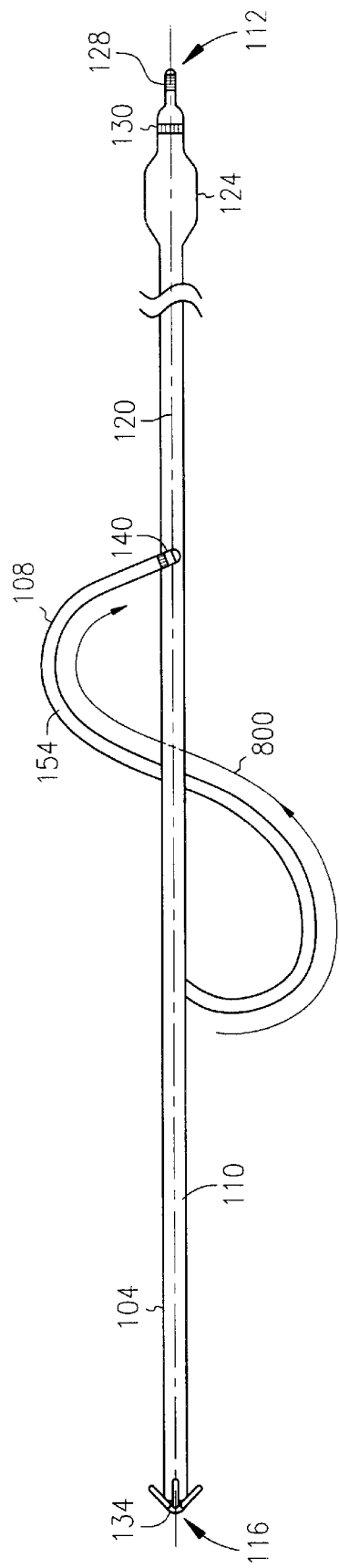
FIG. 8 shows a side view of one exemplary embodiment of a lead according to the present subject matter.

In an additional embodiment, the curve in the transverse lead 108 forms a helix which extends along the longitudinal axis 120 of the main lead 104. FIG. 8 is an exemplary embodiment of the transverse lead 108 in the shape of a helix 800. In one embodiment, the helix 800 extends towards proximal end 112 of the main lead body 110. Alternatively, the helix 800 extends towards distal end 116 of the main lead body 110. The curve, including the helix 800, is formed in any number of ways. For example, the curve is created during the molding or casting of the transverse lead 108. Alternatively, the lead conductor within the lead 108 is structured (e.g., wound) to impart the curve.

Additionally, the main lead 104 and the transverse lead 108 are either created by molding the two leads in a single process or by forming each lead separately and then joining the two leads. For example, lead 104 and lead 108 are formed in a single molding process. Alternatively, the main lead 104 and the transverse lead 108 are created separately. The transverse lead 108 and the main lead 104 are then joined. In one embodiment, lead conductor within the transverse lead 108 are coupled to corresponding lead conductors within the main lead 104. The two leads 104 and 108 are joined by glueing together the lead bodies of the transverse lead 108 and the main lead 104. Alternatively, after coupling the lead conductors of the transverse lead 108 and the main lead 104, the lead bodies of the two leads are welded together (e.g., sonic welding).

Figure 9:
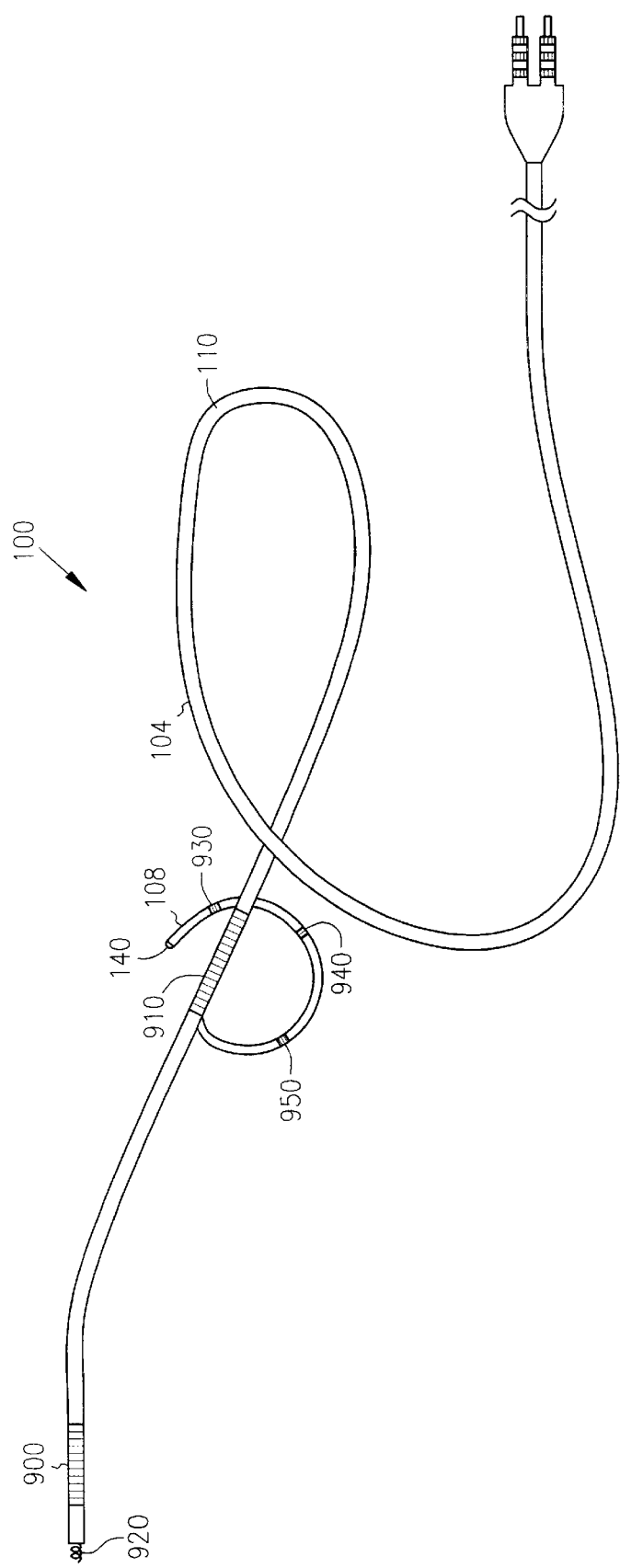
FIG. 9 shows a side view of one exemplary embodiment of a lead according to the present subject matter.

FIG. 9 shows an additional exemplary embodiment of the present invention. The lead 100 shown in FIG. 9 includes elements similar to those in the previous Figures, but the lead 100 in FIG. 9 further includes a first defibrillation electrode 900 and a second defibrillation electrode 910 positioned on the peripheral surface of the main lead 104. In one embodiment, the first defibrillation electrode 900 and the second defibrillation electrode 910 are spaced apart such that when the lead 100 is implanted in a heart, the first defibrillation electrode 900 is positioned in the right ventricle, the second defibrillation electrode 910 is positioned in the right atrium or major vein leading to the right atrium (e.g., superior vena cava), and the transverse lead 108 is implanted in the supraventricular region of the heart. In one embodiment, the first and second defibrillation electrodes 900 and 910 are defibrillation coil electrodes. The lead 100 in FIG. 9 also shows an active fixation screw 920 located at the distal end 116 to allow the main lead 104 to be secured to the endocardial tissue.

In the embodiment of FIG. 9, the transverse lead 108 extends laterally from the main lead body between the proximal end and the distal end and curves around the longitudinal axis to partially encircle at least a portion of the main lead. The transverse lead 108 is positioned on the lead 100 such that when the main lead 104 is implanted with the distal end 116 in the right ventricle the transverse lead 108 is positioned in the supraventricular region of the heart. This allows for cardiac signals to be sensed from and pacing pulses, cardioversion pulses and/or defibrillation pulses to be delivered to either the right ventricle and/or the right atrium.

In an additional embodiment, the transverse lead 108 extends from the main lead 104 at a point between the first defibrillation electrode 900 and the second defibrillation electrode 910. The transverse lead 108 includes the first electrode 140, a second electrode 930, a third electrode 940 and a fourth electrode 950. In one embodiment, the first, second, third, and fourth electrodes 140, 930, 940 and 950 are pacing/sensing ring electrodes. Alternatively, the first, second, third, and fourth electrodes need not be the same type of electrodes. For example, the first electrode 140 is a tip electrode located at the distal end of the transverse lead 108. In one embodiment, the transverse lead 108 extends from and encircles at least a portion of the main lead 104 in such a way that the first, second, third and fourth electrodes 140, 930, 940 and 950 are in a plane that is perpendicular to the longitudinal axis 120 of the main lead body 110 (e.g., similar to perpendicular plane 500 shown in FIG. 5).

Figure 10:
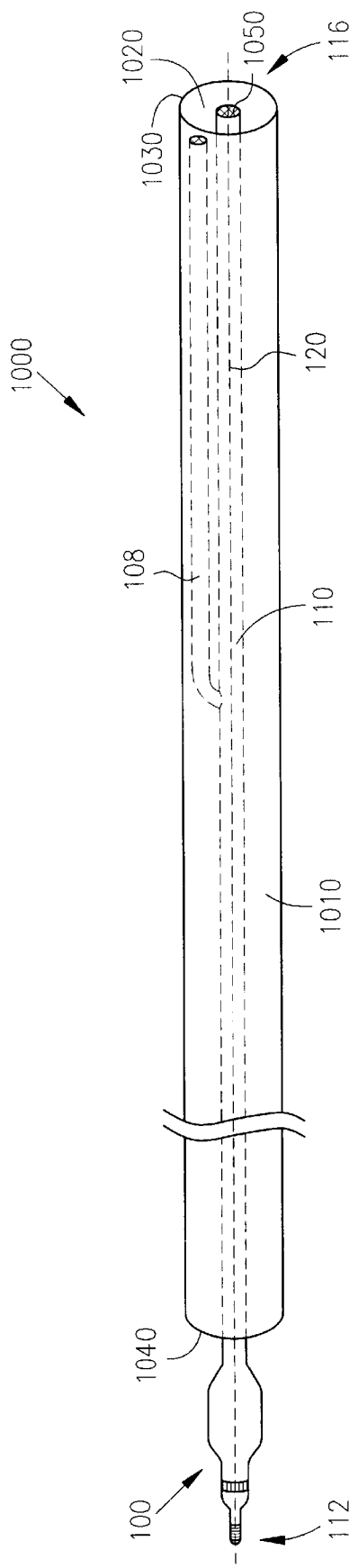
FIG. 10 shows a side view of one exemplary embodiment of a system which includes a lead and an implant catheter according to the present subject matter.

FIG. 10 shows an additional embodiment of a system 1000 according to the present subject matter. The system includes the lead 100 and an implant catheter 1010. In one embodiment, the lead 100 is any one of the leads 100 as previously described or suggested. The implant catheter 1010 includes a lumen 1020 which is of sufficient size to receive and pass at least a portion of the lead 100. For example, the exemplary embodiment shown in FIG. 10 has at least a portion of the main lead 104 and at least a portion of the transverse lead 108 within the lumen 1020 of the implant catheter 1010. The lumen 1020 is of sufficient diameter to allow the implant catheter 1010 to pass over the lead 100.

The exemplary embodiment of system 1000 is shown with the transverse lead 108 lays, or is positioned, parallel with the longitudinal axis 120 and toward the distal end 116 of the main lead body 110 when housed within the implant catheter 1010. In an alternative embodiment, the transverse lead 108 is positioned parallel with the longitudinal axis 120 and toward the proximal end 112 of the main lead 104. In an additional embodiment, the transverse lead 108 spirals, or is wrapped, around the main lead body 110 when housed within the implant catheter 1010 with the distal end of the transverse lead 108 extending either towards the distal end 116 or the proximal end 112 of the main lead body 110.

In one embodiment, the implant catheter 1010 has a wall 1030 which defines the lumen 1020. In one embodiment, the lumen 1020 is circular. Alternatively, the lumen 1020 is non-circular (e.g., having an oval cross-section). Additionally, the length of the implant catheter 1010 is dependent upon the patient the system 1000 is being used with. In addition, the wall 1030 of the implant catheter 1010 optionally includes at least one pre-stressed, or weakened area (e.g., thickness of the wall 1030 being reduced) which extends between the proximal and distal ends of the catheter 1010 to allow the catheter to be split, or peeled, open as the catheter is being withdrawn during the lead 100 implant, as will be described more fully below.

Figure 11:
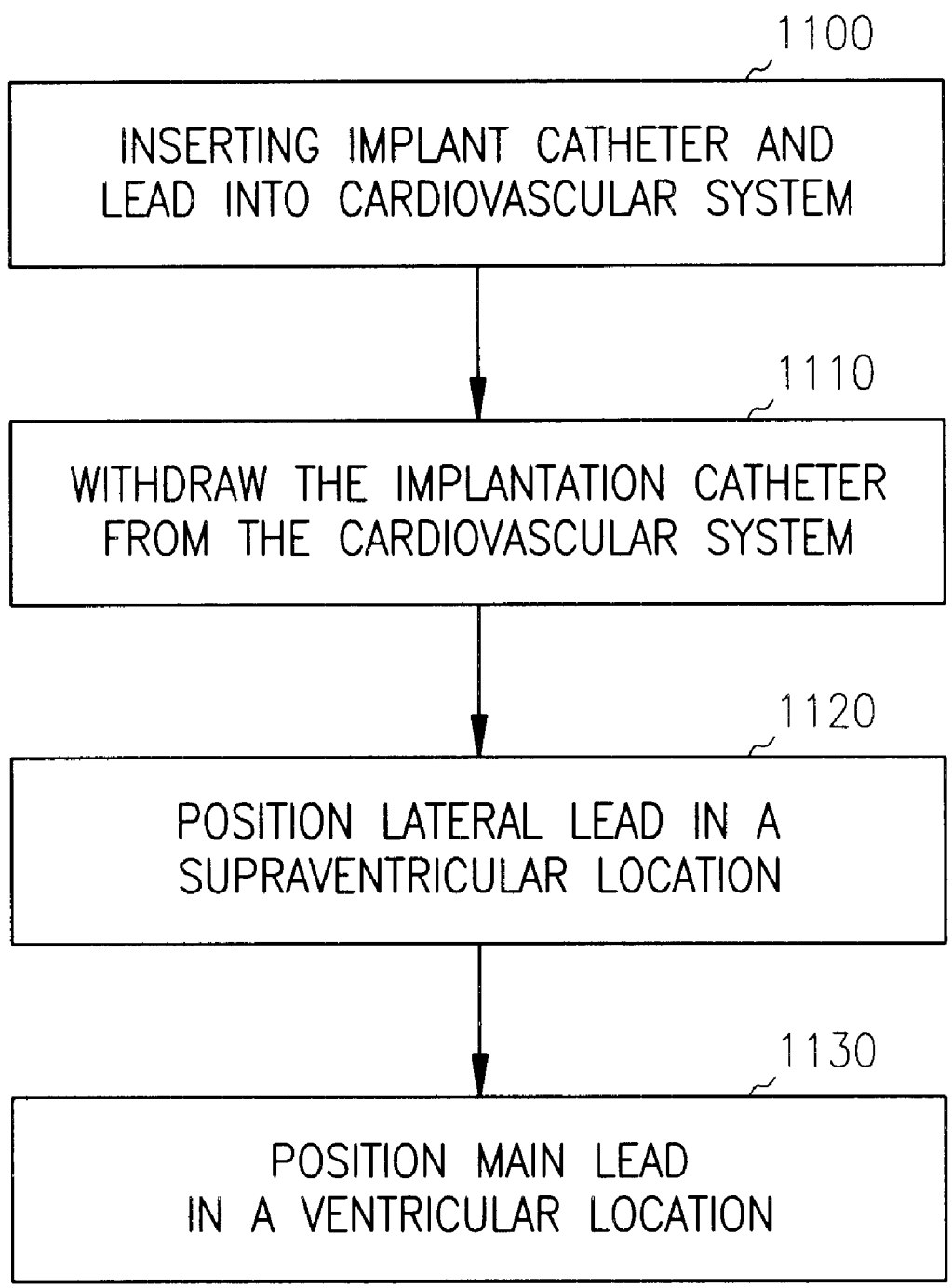
FIG. 11 shows one exemplary embodiment of a method according to the present subject matter.

FIG. 11 shows one exemplary embodiment of a method according to the present invention. At 1100, the implant catheter 1010 and the lead 100 are inserted into the cardiovascular system. In one embodiment, the system of the lead 100 and the implant catheter 1010, where the lead 100 is within the lumen 1020 of the implant catheter 1010, are inserted into subclavicular vein or cephalic vein. The system is then advanced into the right atrium of the heart to a suitable location prior to removing the implant catheter 1010. In one embodiment, a suitable location for the lead 100 is when the distal end 116 of the main lead body 110 reaches the tricuspid valve. Alternatively, the suitable location of the lead 100 is when the proximal end of the first defibrillation electrode reaches the tricuspid valve.

At 1110, once the lead 100 reaches a suitable location within the right atrium the implant catheter 1010 is slid over the lead 100 and withdrawn from the cardiovascular system. In one embodiment, the implant catheter 1010 is peeled open along a pre-stressed, or weakened area, which extends between the proximal and distal ends 140 and 1050 of the implant catheter 1010. One example is where a first pre-stressed, or weakened area (e.g., areas of reduced thickness in the wall 1030 of the catheter 1010) is located on the catheter 1010 to allow the catheter 1010 to be split open so as to allow the catheter to pass around the lead 100 as the catheter is being removed from the vasculature. In an additional example, a second pre-stressed, or weakened area (e.g., areas of reduced thickness in the wall 1030 of the catheter 1010) is included along with the first to allow the catheter 1010 to be split into two pieces as it is being removed from the vasculature.

Figure 12:
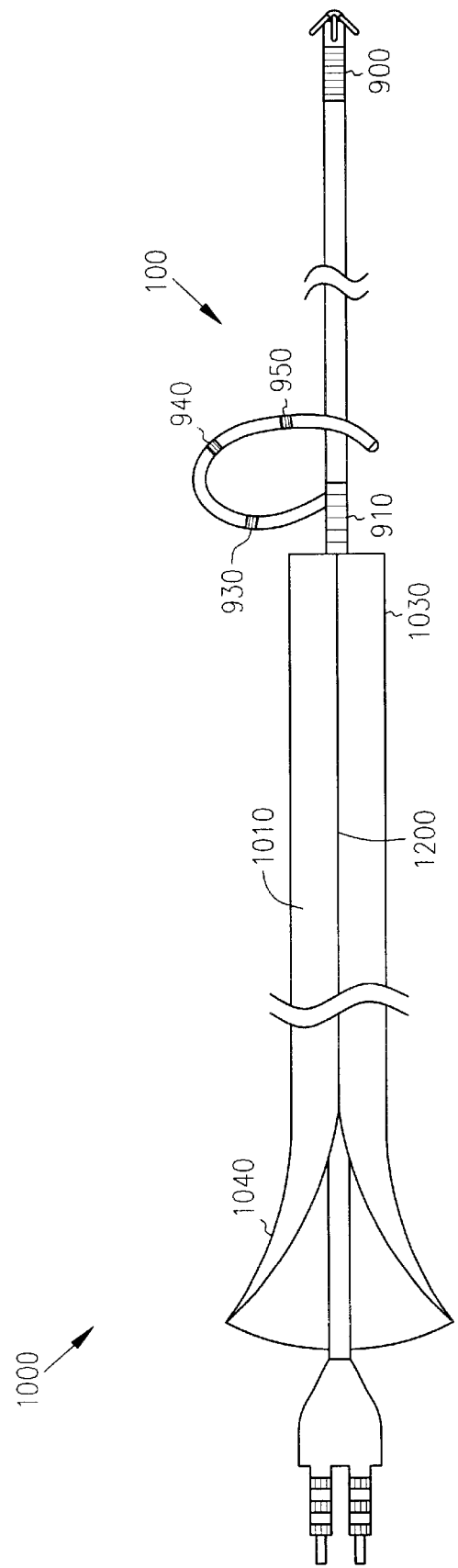
FIG. 12 shows a side view of one exemplary embodiment of a system which includes a lead and an implant catheter according to the present subject matter.

FIG. 12 shows one exemplary embodiment of the system 1000 where the implant catheter 1010 includes a first pre-stressed area 1200. As FIG. 12 shows, the implant catheter 1010 is split open along the first pre-stressed area 1200 to allow the implant catheter 1010 to be removed from around the lead 100. In one embodiment, the material of the implant catheter 1010 is adapted to be torn along the first pre-stressed area 1200.

Referring again to FIG. 11, once the implant catheter 1010 has been removed, the transverse lead 108 is positioned in a supraventricular location, at 1120. In one embodiment, as the implant catheter 1010 passes over the lead 100, the transverse lead 108 retakes its curved shape, as shown in FIGS. 3 and 12, extending out and away from the main lead body 110 to press the at least one electrode onto the endocardial surface of the right atrium. In this position, the electrodes on the transverse lead 108 are used to sense one or more cardiac signals (e.g., unipolar signals and/or bipolar signals) from the right atrium. In an alternative embodiment, the transverse lead 108 is inserted at least partially into the coronary sinus vein to allow pacing and sensing to occur from a position that is adjacent the left atrium or from the left ventricle (when the transverse lead 108 is advanced through the coronary sinus vein into the great cardiac vein). In this embodiment, the transverse lead 108 further includes a lumen which is adapted to receive a stylet inserted through the main lead 104 which is used to guide the lead 108. Once positioned within the coronary sinus and any additional segments of the coronary veins, the stylet is removed to allow the transverse lead 108 to resume a relaxed configuration. In one embodiment, the relaxed configuration of the lead 108 is adapted to closely resemble the physical structure of the coronary veins into which the lead 108 is intended to be placed.

Once the transverse lead 108 is positioned, the main lead is positioned in a ventricular location at 1130. In one embodiment, a stylet is used to advance the distal end 116 of the main lead 104 into the ventricular location. In one embodiment, the distal end 116 of the main lead 104 is implanted into the apex of the right ventricle, where the main lead 104 is secured in the right ventricle by either by passive (e.g., tines) or an active (e.g., screw tip) fixation. The proximal end 112 of the lead is held and the stylet is then withdrawn from the lead 100. The lead 100 is then connected to the implantable pulse generator for use in the patient. One or more cardiac signals are then sensed using the distal tip pace/sense electrode 134 on the main lead 104.

The lead and system of the present invention provide for several advantages. For example, because the lead 100 is implanted with an implant catheter, the lead 100 is implanted with only a single pass. This saves time by also allowing for the diameter of the lead 100 (e.g., main lead body 110 and the transverse lead body 154) to have smaller diameters as compared to other lead bodies, as the implant catheter is used to provide support and pushability to the system. This means that a more flexible and a smaller lead is implanted into the patient. In addition, because the transverse lead 108 extends from the main lead body 110 there is better lead abrasion performance (i.e., less lead-on-lead contact) as compared to a system where two or more individual and entirely separate leads are implanted.

Figure 13:
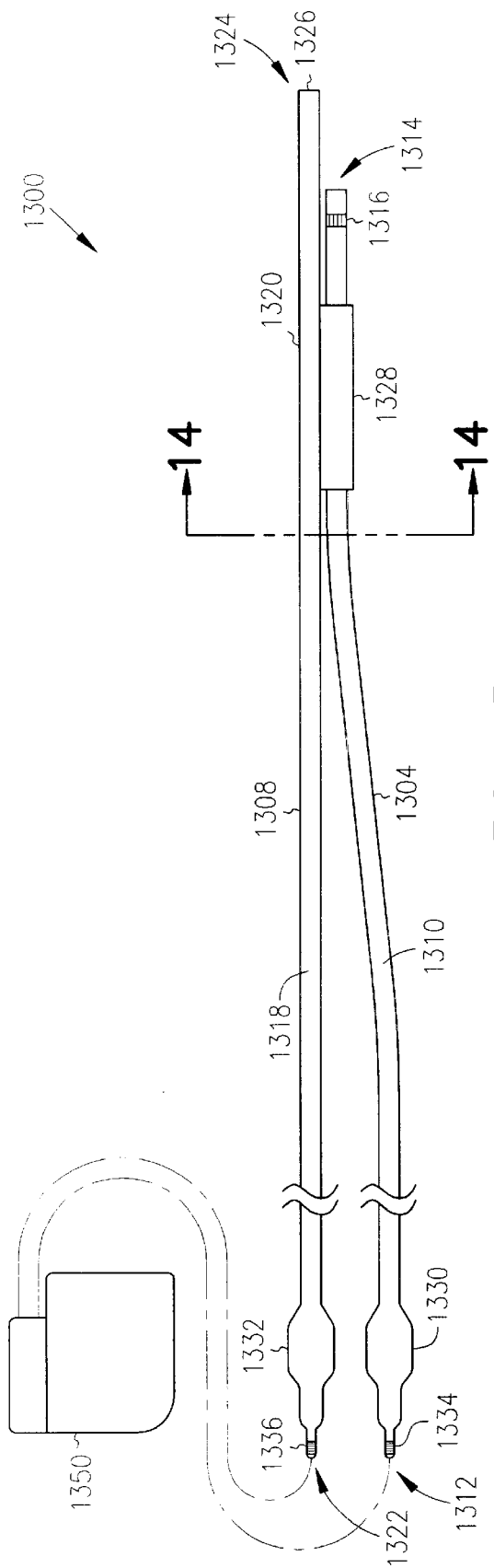
FIG. 13 shows a side view of an additional exemplary embodiment of a lead system according to the present subject matter.

FIG. 13 shows an additional exemplary embodiment of a lead system 1300 according to the present invention. The lead system 1300 includes a first lead 1304 and a second lead 1308. The first lead 1304 includes a lead body 1310 having a proximal end 1312, a distal end 1314 and at least one electrode. FIG. 13 shows the first lead 1304 having a first pace/sense electrode 1316. In one embodiment, the first pace/sense electrode 1316 is a ring electrode, where the ring electrode at least partially or completely encircles the lead body 1310.

The second lead 1308 includes a lead body 1318 having an external surface 1320, a proximal end 1322, a distal end 1324 and at least one electrode. In one embodiment, the second lead 1308 includes a sense/pace electrode 1326 and a sleeve 1328 through which at least a portion of the lead body 1310 of the first lead 1304 freely passes, or moves, to attach the first lead 1304 to the second lead 1308. In one embodiment, the sense/pace electrode 1326 is a distal tip sense/pace electrode.

Sleeve 1328 is coupled to the second lead 1308. In one embodiment, the sleeve 1328 is coupled to the external surface 1320 of second lead 1308. For example, the sleeve 1328 is glued or bonded to the external surface 1320 of the second lead 1308. Alternatively, both the sleeve 1328 and the second lead 1308 are cast or molded so they both have an integral construction. In an alternative embodiment, the sleeve 1328 is constructed of a bioabsorbable material. For example, the sleeve 1328 is constructed of a polylactic acid, which allows for the sleeve 1328 to be absorbed by the body after implant.

The sleeve 1328 is a tubular segment having an inner surface defining an opening adapted to receive and pass at least a portion of the lead body 1310 of the first lead 1304. In one embodiment, the tubular segment of the sleeve 1328 is cylindrical and the opening has a diameter that is larger than the outer diameter of the lead body 1310 of the first lead 1304. In one embodiment, the inner surface of the sleeve 1328 includes a lubricious coating which allows the first lead 1304 to pass more freely through the sleeve 1328 as compared the sleeve 1328 without the lubricious coating.

The first lead 1304 includes a lead connector 1330 having one or more connector terminals near or at the proximal end 1312. The second lead 1308 also includes a lead connector 1332 having one or more connector terminals at or near the proximal end 1322. In one embodiment, the lead connectors 1312 and 1322 and connector terminals are designed to conform with International Standards (e.g., IS-1 UNI or IS-1 BI).

In one embodiment, the first lead 1304 has a connector terminal pin 1334 which is electrically connected to the ring electrode 1316. The second lead 1308 also includes a connector terminal pin 1336 which is electrically connected to the distal tip sense/pace electrode 1326. In an additional embodiment, the first lead 1304 and the second lead 1308 include additional pace/sense electrodes (e.g., tip and/or ring electrodes) and/or defibrillation electrodes to allow for unipolar and/or bipolar cardiac signals to be sensed and for pacing, cardioversion, and/or defibrillation electrical energy to be delivered through either the first lead 1304 and/or second lead 1308. In addition, both the first lead 1304 and/or the second lead 1308 optionally include a lumen to receive either a stylet or a guidewire which are used in implanting both the first lead 1304 and the second lead 1308. In one embodiment, the lumen is formed in each of the first and second leads from a lead conductor which connects the electrode 1316 or 1326 with the connector pin 1334 or 1336.

In one embodiment, the lead connectors 1330 and 1332 are adapted to be releasably coupled to a connector block of an implantable pulse generator 1350. In one embodiment, the implantable pulse generator 1350 contain electronics to sense cardiac signals from the heart through the use of the electrodes on the leads 1304 and 1308, where the cardiac signals include indications of cardiac cycles. In one embodiment, a unipolar cardiac signal is sensed between the first pace/sense electrode 1316 on the first lead 1304 and the housing of the implantable pulse generator 1350. A unipolar cardiac signal is also sensed between the pace/sense electrode 1326 on the second lead 1308 and the housing of the implantable pulse generator 1350. Alteratively, additional pacing/sensing electrodes are provided on the first lead 1304 and/or the second lead 1308 to allow for bipolar cardiac signals to be sensed from the heart.

In one embodiment, the pace/sense electrode 1326 on the second lead 1308 is a porous electrode, where the porous electrode include woven mesh electrode or electrode created by sintering metal powders or microspheres onto metal substrates. The pacing/sensing electrodes are created from either platinum, platinum-iridium alloys or alloys which can include cobalt, iron, chromium, molybdenum, nickel and/or manganese.

In one embodiment, the first and second lead bodies 1310 and 1318 are formed of a biocompatible polymer such as silicone rubber and/or polyurethane. The first and second leads 1304 and 1308 each include one or more lumens which are adapted to receive a stylet or guidewire for guiding and implanting the lead. In one embodiment, the first and second leads 1304 and 1308 each include a first lumen, where the first lumen extends from an opening at the proximal end 1312 and 1322 to the distal end 1314 and 1324 to allow the leads 1304 and 1308 to be controlled through the use of the stylet or guidewire. As previously discussed, in one exemplary embodiment the lumen is formed from the lead conductor which connects the pace/sense electrode and the connector pin.

The first lead 1304 and the second lead 1308 each has a length and a shape that is adapted to be implanted into any number of size hearts. The length of the first lead is be dependent upon the size of the patient. In one embodiment, the length of the first lead is sufficient to allow the distal end 1314 of the first lead 1304 to be implanted in a supraventricular location of the heart. In one embodiment, the distal end 1314 and the first pace/sense electrode 1316 of the first lead 1304 are implanted into the right atrium. Alternatively, the distal end 1314 and the first pace/sense electrode 1316 of the first lead 1304 are positioned adjacent the left atrium by inserting the first lead 1304 through the coronary sinus vein. Additionally, the distal end 1314 and the first pace/sense electrode 1316 of the first lead 1304 first lead 1304 are implanted adjacent the left ventricle by inserting the first lead 1304 through the coronary sinus and into the great cardiac vein.

In one embodiment, the length of the second lead is be dependent upon the size of the patient. In one embodiment, the length of the second lead is sufficient to allow the distal end 1324 of the second lead 1308 to be implanted in a ventricular location of the heart. In one embodiment, the distal end 1324 and the pace/sense electrode 1326 of the second lead 1308 are implanted into the apex of the right ventricle. In one embodiment, the sleeve 1328 is positioned along the second lead 1308 so that the sleeve 1328 is located in the right atrium or major vein leading to the right atrium (e.g., superior vena cava) when the second lead 1308 is implanted in the right ventricle.

The second lead 1308 is attached to the endocardium either actively or passively. For active fixation the second lead 1308 has an active screw at the distal end 1324 of the lead body 1318, where the screw is either retractable or not retractable, and either electrically active or not electrically active. For passive fixation tines are positioned behind the electrode and are adapted to become entangled/entrapped within the trabeculae of the right ventricle. The first lead 1304 is passively coupled to either the endocardium or to a coronary vein of the heart. In one embodiment, the first lead 1304 includes tines at the distal end 1314. Alternatively, the lead body 1310 includes lateral deflections (e.g., a zig-zag) which helps to secure the first lead 1304 in the coronary sinus or other coronary vein of the heart.

In an alternative embodiment, the length of the second lead is sufficient to allow the distal end 1324 of the second lead 1308 to be implanted in a supraventricular location of the heart. In one embodiment, the distal end 1324 and the pace/sense electrode 1326 of the second lead 1308 are implanted into the right atrium, where the second lead 1308 is attached to the endocardium either actively or passively. For active fixation the second lead 1308 has an active screw at the distal end 1324 of the lead body 1318, where the screw is either retractable or not retractable, and either electrically active or not electrically active. For passive fixation tines are positioned behind the electrode and are adapted to become entangled/entrapped within the trabeculae of the right atrial appendage. In one embodiment, the second lead 1308 has a J-shape as will be described more fully below.

Figure 14:
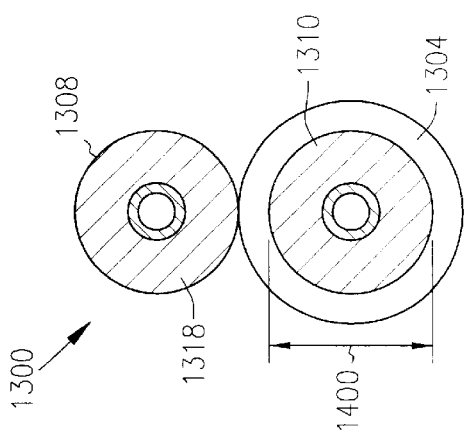
FIG. 14 shows a view of the lead system of FIG. 13 taken along the lines 14—14.

FIG. 14 shows an embodiment of the first lead 1304 passing through the sleeve 1328. As shown, the size of the opening 1400 through the sleeve 1328 is of sufficient size to allow the lead body 1310 to pass into and out of the sleeve 1328. In one embodiment, the first lead 1304 is pushed through the opening 1400 of the sleeve 1328, and if needed the first lead 1304 is pulled back through the opening 1300 of the sleeve 1328.

Figure 15:
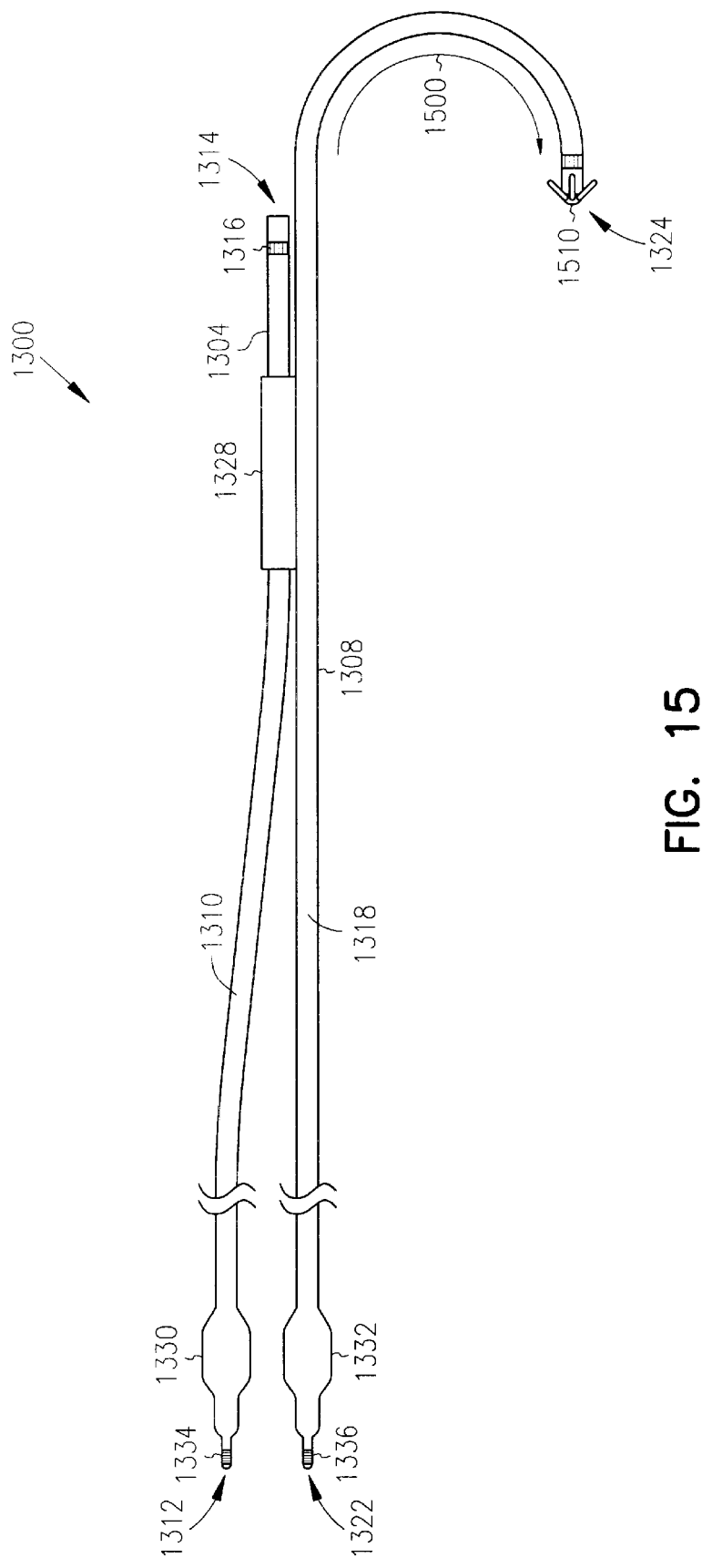
FIG. 15 shows a side view of an additional exemplary embodiment of a lead system according to the present subject matter.

FIG. 15 shows an additional exemplary embodiment of the lead system 1300 according to the present invention. The lead system includes the first lead 1304 and the second lead 1308. In one embodiment, the first and second leads 1304 and 1308 are as previously described or suggested. In addition, the second lead 1308 has a J-shape 1500. In one embodiment, the second lead 1308 having the J-shape 1500 is used as a right atrium lead. As previously described, additional embodiments of the second lead 1308 include additional electrodes which allow for bipolar sensing of cardiac signals and either active or passive fixation of the second cardiac lead 1308. In the embodiment shown in FIG. 15, the second lead 1308 is shown having passive fixation tines 1510.

Figure 16:
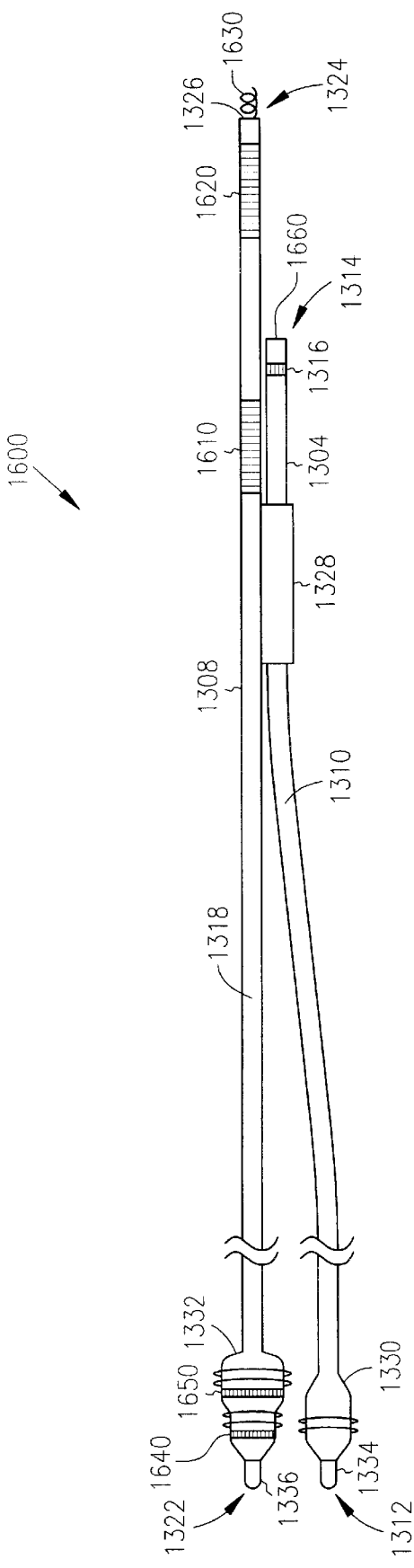
FIG. 16 shows a side view of another exemplary embodiment of a lead system according to the present subject matter.

FIG. 16 shows another exemplary embodiment of a lead system 1600 according to the present invention. The lead system 1600 includes elements similar to those described for the first lead 1304 and the second lead 1308, but the lead system 1600 further includes a first defibrillation electrode 1610 and a second defibrillation electrode 1620 positioned on the peripheral surface of the second lead 1308. In one embodiment, the first defibrillation electrode 1610 and the second defibrillation electrode 1620 are spaced apart such that when the second lead 1308 is implanted in a heart, the first defibrillation electrode 1610 is positioned in the right ventricle and the second defibrillation electrode 1620 is positioned in the right atrium or major vein leading to the right atrium (e.g., superior vena cava). In one embodiment, the first and second defibrillation electrodes 1610 and 1620 are defibrillation coil electrodes. The second lead 1308 in FIG. 16 also shows an active fixation screw 1630 located at the distal end 1324 to allow the second lead 1308 to be secured to the endocardial tissue.

In the embodiment of FIG. 16, the sleeve 1328 is positioned along the second lead 1308 so that the sleeve 1328 is located in the right atrium or major vein leading to the right atrium (e.g., superior vena cava) when the distal end 1324 of the second lead 1308 is implanted in the right ventricle. In one embodiment, the sleeve 1328 is positioned proximal the first defibrillation electrode 1610. In an alternative embodiment, the sleeve 1328 is positioned between the first defibrillation electrode 1610 and the second defibrillation electrode 1620. Additional connector rings 1640 and 1650 are also included at the lead connector 1332, where the connector ring 1640 is coupled to the first defibrillation electrode 1610 and the connector ring 1650 is coupled to the second defibrillation electrode 1620. Lead system 1600 also includes a second pace/sense electrode 1660 on the first lead 1304. In one embodiment, the second pace/sense electrode 1660 is a distal tip electrode which allows for a bipolar cardiac signal to be sensed between the second pace/sense electrode 1660 and the first pace/sense electrode 1316 on the first lead 1304.

Figure 17:
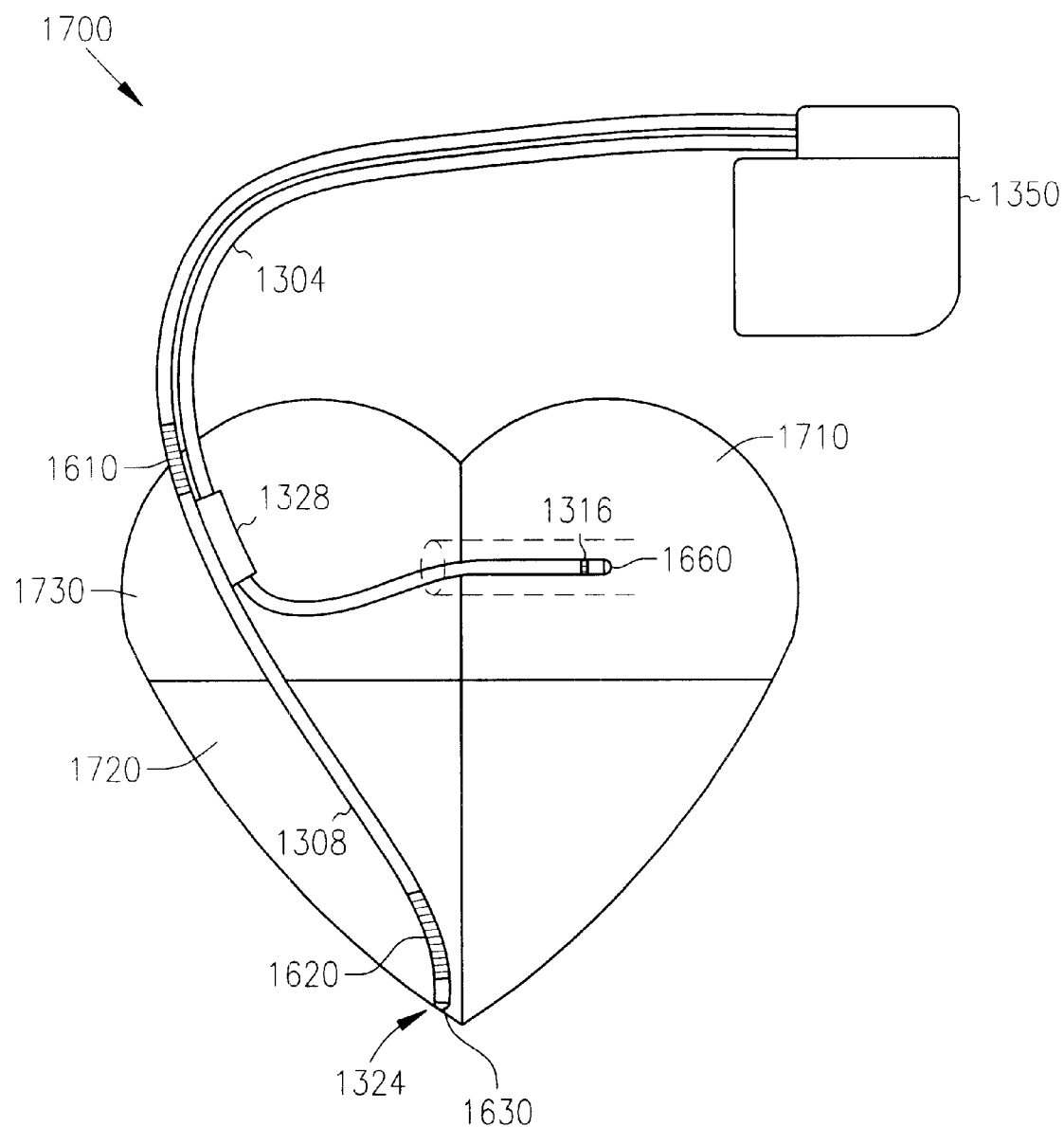
FIG. 17 shows a side view of one exemplary embodiment of a lead system implanted into a heart from which segments have been removed to show details.

FIG. 17 shows one exemplary embodiment of the lead system 1600 implanted into a heart 1700. As FIG. 17 shows, the first lead 1304 is implanted into the vasculature with the first pace/sense electrode 1316 and the second pace/sense electrode 1660 positioned adjacent the left atrium 1710. The sleeve 1328 is shown positioned on the second lead 1308 such that when the distal end 1324 of the second lead 1308 is implanted in the right ventricle 1720 the sleeve 1328 is in the right atrium 1730.

Figure 18:
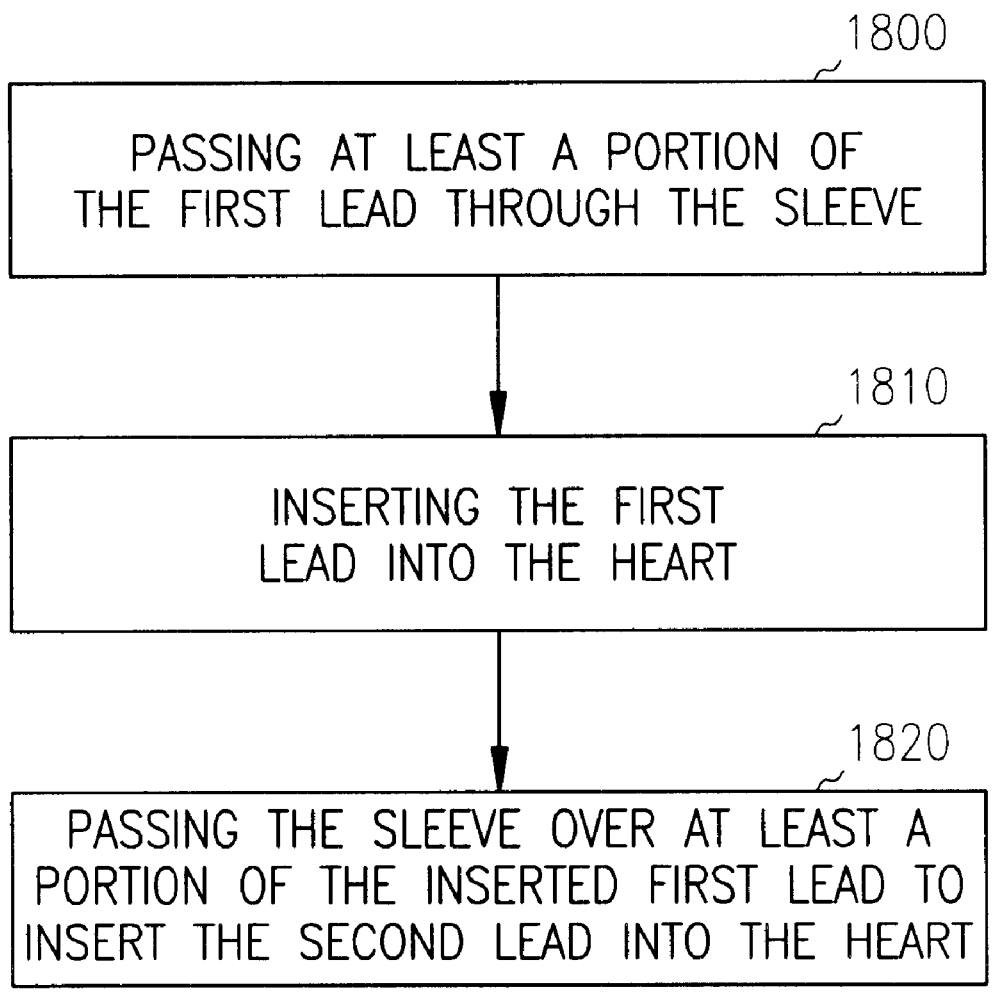
FIG. 18 shows a side view of one exemplary embodiment of a method according to the present subject matter.

FIG. 18 shows one exemplary embodiment of a method according to the present invention. At 1800, at least a portion of the first lead 1304 is passed through the sleeve 1328. At 1810, the first lead 1304 is then inserted into the heart. In one embodiment, the first lead 1304 is inserted into a supraventricular region of the heart, where the supraventricular region includes the coronary sinus vein of the heart.

In one embodiment, inserting the first lead 1304 into the heart includes inserting a stylet into the lumen of the first lead 1304 and guiding the first lead into the heart through the use of the stylet. In an alternative embodiment, the first lead 1304 is inserted into the heart by first inserting a guidewire into the heart. In one embodiment, the guidewire is positioned within the coronary sinus vein, great cardiac vein or branch veins from either of these veins. The first lead 1304 is then advanced over the guidewire to position the first lead 1304 in the heart, with the distal end of the first lead 1304 in either the right atrium, the coronary sinus vein, great cardiac vein or branching vein.

In one embodiment, the lumen of the first lead 1304 extends between and has openings at the distal end 1314 and the proximal end 1312 to allow the guidewire to pass through the lumen of the first lead 1304 to allow for an over-the-wire insertion of the first lead 1304. The first lead 1304 is then positioned in either the right atrium, coronary sinus, great cardiac vein or branching vein.

At 1820, the sleeve 1328 is then passed over at least a portion of the inserted first lead 1304 to insert the second lead 1308 into the heart. In one embodiment, a stylet is used to advance the second lead 1308 into the heart, and positioned as previously described. In one embodiment, the sleeve is passed over at least the portion of the inserted first lead 1304 to implant the distal end 1324 of the second lead 1308 in the right ventricle of the heart. In one embodiment, the distal end 1324 of the second lead 1308 is secured in the right ventricle by either by passive (e.g., tines) or an active (e.g., screw tip) fixation. Additionally, the distal end of the first lead 1304 is secured through passive fixation (e.g., tines or lateral deflections in the lead body 1310 which press the lead 1304 against the cardiac vein) The proximal ends 1312 and 1322 are then held and the stylet and guidewire withdrawn. The leads 1304 and 1308 are then connected to the implantable pulse generator for use in the patient.

The lead and system of the present invention provide for several advantages. For example, because the leads 1304 and 1308 are coupled through the sleeve 1328, the lead are implanted with only a single pass, thus saving time during lead implant. In addition, because the first and second leads 1304 and 1308 are coupled through the sleeve 1328 there is better lead abrasion performance (i.e., less lead-on-lead contact) as compared to a system where two or more individual and entirely separate leads are implanted.

It is to be understood that the above description is intended to be illustrative, and not restrictive. Many other embodiments will be apparent to those of skill in the art upon reading and understanding the above description. For example, the present invention can be used with a variety of medical devices. Additionally, the Figures showing the exemplary embodiments herein are not to scale. Although the use of the lead has been described for use in a cardiac pacing system, the lead could also be applied to other types of body stimulating systems. The scope of the invention should, therefore, be determined with reference to the appended claims, along with the full scope of equivalents to which such claims are entitled.

What is claimed is:

1. A lead comprising:

a main lead having a main lead body with a longitudinal axis and at least one electrode, where the main lead body extends from a proximal end to a distal end; and a transverse lead having a transverse lead body and at least one electrode, where the transverse lead body extends helically from the main lead body between the proximal end and the distal end at least once around the main lead body.

2. The lead of claim 1, where the transverse lead extends toward the proximal end of the main lead body.

3. The lead of claim 1, where transverse lead body extends toward the distal end of the main lead body.

4. The lead of claim 1, where at least a portion of the main lead and at least a portion of the transverse lead are both adapted to be housed within an implant catheter.

5. The lead of claim 1, where the at least one electrode of the main lead includes a first defibrillation electrode and a second defibrillation electrode.

6. The lead of claim 5, where transverse lead emanates from the main lead between the first defibrillation electrode and the second defibrillation electrode.

7. The lead of claim 6, where the transverse lead includes a first electrode, a second electrode, a third electrode and a fourth electrode.

8. A system comprising:

a main lead having a main lead body with a longitudinal axis and at least one electrode, where the main lead body extends from a proximal end to a distal end;

a transverse lead having a transverse lead body, a proximal end, a distal end and at least one electrode, where the transverse lead body extends laterally from the main lead body around the longitudinal axis to partially encircle at least a portion of the main lead; and an implant catheter, where at least a portion of the main lead and at least a portion of the transverse lead are both adapted to be housed within and pass through the implant catheter, the distal end of the transverse lead body being positioned a radial distance from the longitudinal axis of the main lead body when the transverse lead is not within the catheter and the transverse lead body being spiraled around the main lead body where the transverse lead body extends helically around the main lead body when housed within the implant catheter.

9. The system of claim 8, where the transverse lead body extends toward the proximal end of the main lead body when housed within the implant catheter.

10. The system of claim 8, where the transverse lead body is extends toward the distal end of the main lead body when housed within the implant catheter.

11. A method comprising:

inserting an implantation catheter into a cardiovascular system, where the implantation catheter includes a main lead and a transverse lead extending helically from the main lead at least once around the main lead;

withdrawing the implantation catheter from the cardiovascular system; and positioning a distal end of the transverse lead against endocardial tissue.

12. The method of claim 11, where positioning the transverse lead includes positioning the transverse lead adjacent a left atrium.

13. The method of claim 11, where positioning the transverse lead includes positioning a portion of the transverse lead adjacent a left atrium.

14. The method of claim 11, where positioning the main lead includes positioning the main lead in a right ventricle.

15. The method of claim 11, including sensing one or more cardiac signals with the transverse lead and sensing one or more cardiac signals with the main lead.

16. A lead comprising:

a main lead including a main lead body having a longitudinal axis, a proximal end and a distal end;

a transverse lead including a transverse lead body having a proximal end and a distal end, the transverse lead body extending helically from the main lead body around and along the longitudinal axis of the main lead body; and a first electrode and a second electrode located on the transverse lead body such that the first and second electrodes are spaced along the longitudinal axis of the main lead body.

17. The lead of claim 16, wherein the transverse lead body extends toward the distal end of the main lead body.

18. A lead for insertion into a heart comprising:

a main lead including a main lead body having a longitudinal axis, a proximal end and a distal end;

a transverse lead including a transverse lead body having a proximal end and a distal end, the transverse lead body extending helically from the main lead body;

a first electrode located on the transverse lead body; and a second electrode located on the transverse lead body such that the first and second electrodes are spaced along the longitudinal axis of the main lead body.

19. The lead of claim 18, wherein the first electrode is located on the distal end of the transverse lead body.

20. The lead of claim 18, wherein the transverse lead body becomes concentric with the main lead body as the transverse lead body extends helically around the longitudinal axis.

21. The lead of claim 18, wherein the main lead includes a plurality of electrodes.

22. The lead of claim 21, wherein the transverse lead emanates from the main lead between two electrodes on the main lead.

23. The lead of claim 22, wherein the transverse lead includes a plurality of electrodes.

24. A lead comprising:

a main lead including a main lead body having a longitudinal axis, a proximal end and a distal end;

a first electrode located on the main lead body between the proximal and distal ends of the main lead body;

a transverse lead including a transverse lead body having a proximal end and a distal end, the transverse lead body extending from the main lead body in a continuously helical manner at a uniform helical pitch around the main lead body; and a second electrode located on the transverse lead body between the longitudinal axis of the main lead body and the distal end of the transverse lead body.

25. A lead comprising:

a main lead having a main lead body with a longitudinal axis, where the main lead body extends from a proximal end to a distal end; and a transverse lead having a transverse lead body extending helically from the main lead body between the proximal end and the distal end at least once around the longitudinal axis, where the main lead includes a first electrode and a second electrode such that the transverse lead emanates from the main lead between the first electrode and the second electrode.

26. A method comprising:

inserting an implantation catheter into a cardiovascular system, where the implantation catheter includes a main lead and a transverse lead extending helically around and along a longitudinal axis of the main lead body at a uniform helical pitch;

withdrawing the implantation catheter from the cardiovascular system; and pressing a distal end of the transverse lead against endocardial tissue.

* * * * *